US009678067B2

(12) United States Patent (10) Patent No.: US 9,678,067 B2
Inouye et al. (45) Date of Patent: Jun. 13, 2017

(54) METHOD FOR EXTENDING LIGHT-EMITTING TIME OF CALCIUM-BINDING PHOTOPROTEIN SOLUTION

(75) Inventors: Satoshi Inouye, Yokohama (JP); Satoko Sasaki, Yokohama (JP)

(73) Assignee: JNC Corporation, Tokyo (JP)

( * ) Notice: Subject to any disclaimer, the term of this patent is extended or adjusted under 35 U.S.C. 154(b) by 524 days.

(21) Appl. No.: 11/411,715

(22) Filed: Apr. 26, 2006

(65) Prior Publication Data

US 2006/0246534 A1 Nov. 2, 2006

(30) Foreign Application Priority Data

Apr. 28, 2005 (JP) .................................. 2005-133743

(51) Int. Cl.
*G01N 33/533* (2006.01)
*G01N 33/58* (2006.01)

(52) U.S. Cl.
CPC ......... *G01N 33/533* (2013.01); *G01N 33/582* (2013.01); *G01N 2333/43595* (2013.01)

(58) Field of Classification Search
None
See application file for complete search history.

(56) References Cited

U.S. PATENT DOCUMENTS

| | | | |
|---|---|---|---|
| 5,360,728 A | 11/1994 | Prasher | |
| 5,824,472 A | 10/1998 | Betlach et al. | |
| 2004/0235078 A1 | 11/2004 | Rosen et al. | |
| 2005/0054838 A1 | 3/2005 | Otsuka et al. | |

FOREIGN PATENT DOCUMENTS

| | | |
|---|---|---|
| EP | 1 666 488 A1 | 6/2006 |
| EP | 1666488 A1 * | 6/2006 |
| JP | 61-135586 A | 6/1986 |
| JP | 62-261942 A | 11/1987 |
| JP | 01-132397 A | 5/1989 |
| JP | 3162480 A | 7/1991 |
| JP | 3167288 A | 7/1991 |
| JP | 2000-508075 A | 6/2000 |
| JP | 2001-270899 A | 10/2001 |
| JP | 2004-035449 A | 2/2004 |
| JP | 2004-156017 A | 3/2004 |
| JP | 2006055082 | 3/2006 |
| WO | WO 87/05937 A1 | 10/1987 |
| WO | WO 98/30908 | 7/1998 |
| WO | WO 00/29603 A3 | 5/2000 |
| WO | WO 03/054163 A3 | 7/2003 |
| WO | WO 03/060063 A3 | 7/2003 |
| WO | WO 03/082904 A3 | 10/2003 |
| WO | WO2005/014633 A1 | 2/2005 |
| WO | WO 2005014633 A1 * | 2/2005 |

OTHER PUBLICATIONS

Hoffman, Wilfried; "The basic principles of thermal process safety: Towards a better communication between safety experts and process chemists." in Process chemistry in the pharmaceutical industry, Gadamasetti ed. 1999, isbn 0-8247-1981-6.*
Lowe, Derek, the blog "In the pipeline" (pipeline.corante.com), posted Sep. 18, 2009.*
Darvey, Ivan G. "The steady state kinetics of isotope exchange at equilibrium: one substrate-one product enzymic mechanisms where two molecules of substrate or product are bound to an enzyme molecule." Biochem. J. (1974) 143 p. 783-784.*
Smith, Stephen J. and Zucker, Robert S.; "Aequorin response facilitation and intracellular calcium accumulation in molluscan neurones." J. Physiol. (1980) 300 p. 167-196.*
Li-Smerin, Yingying et al; "Free intracellular Mg2+ concentration and inhibition of nmda responses in cultured rat neurons." J. Physiol (2001) 533.3 p. 729-743.*
Shimomura, Osamu and Johnson, Frank H.; "Peroxidized coelenterazine, the active group in the photoprotein aequorin." Proc. Natl. Acad. Sci. USA (1978) 75(6) p. 2611-2615.*
Goto, T. "Bioluminescence of marine organisms" in "Marine Natural Products," Sheuer, Paul ed. (1980) ISBN 0-12-624003-05.*
Cameron, Frank K. and Seidell, Atherton, "Solubility of gypsum in aqueous solutions of certain electrolytes." J. Phys. Chem. (1901) 5(9) p. 643-655.*
The BBC website bitesize (http://www.bbc.co.uk/schools/gcsebitesize/science/add_edexcel/ionic_compounds/ionicanalysisrev2.shtml, downloaded Mar. 1, 2016.*
Comsol.com, https://www.comsol.com/multiphysics/diffusion-equation, downloaded Mar. 1, 2016.*
Perrin, D. D. and DEmpsy, Boyd, "Metal-ion buffers" in Buffers for pH and metal ion control (1974) ISBN 978-0-412-21890-3, chapter 7.*
Schock, Michael R. et al, "Effect of pH, dic, orthophosphate and sulfate on drinking water cuprosolvency." in EPA document EPA/600/R-95/085 (1995) p. 61.*
Bondar et al., "Cadmium-Induced Luminescence of Recombinant Photoprotein Obelin," *Biochimica of Biophysica Acta*, 1231: 29-32 (1995).
Deng et al., "Structural Basis for the Emission of Violet Bioluminescence from a W92F Obelin Mutant," *FEBS Letters*, 506(3): 281-285 (Oct. 12, 2001).
Head et al., "The Crystal Structure of the Photoprotein Aequorin at 2.3 A Resolution," *Nature*, 405(6784): 372-376 (May 18, 2000).
Inouye et al., "Cloning and Sequence Analysis of cDNA for the Luminescent Protein Aequorin," *Proc. Natl. Acad. Sci. USA*, 82(10): 3154-3158 (May 1985).
Stephenson et al., "Studies on the Luminescent Response of the $Ca^{2+}$-Activated Photoprotein, Obelin," *Biochimica et Biophysica Acta*, 678: 65-75 (1981).

(Continued)

*Primary Examiner* — Fred Reynolds
(74) *Attorney, Agent, or Firm* — Leydig, Voit & Mayer, Ltd.

(57) ABSTRACT

Methods for extending light-emitting time of a solution of a calcium-binding photoprotein that instantaneously emits light by binding to calcium ions are provided. In the light-emitting reaction system of a solution of a calcium-binding photoprotein, a light-emitting reaction is performed in the presence of an anion capable of binding to the calcium ion or the cation that can be substituted for the calcium ion and/or a cation that can bind to the calcium-binding site of the calcium-binding photoprotein with a lower affinity than the calcium ion or the cation that can be substituted for the calcium ion without activating the calcium-binding photoprotein.

14 Claims, 5 Drawing Sheets

(56) References Cited

OTHER PUBLICATIONS

Jena Bioscience, "Crystallization screens—JBScreen PEG/Salt, 2004," available at http://www.jenabioscience.com/index.php/5314c472c8c9389eb2e90848aba236cd/1/catalog/1005 (Retrieved Feb. 3, 2007).

The Patent Office: Patents Directorate, Search Report under Section 17(6), dated Mar. 12, 2007.

Huang et al., "Identification and characterization of a catalytic base in bacterial luciferase by chemical rescue of a dark mutant," *Biochemistry*, V. 36, No. 48, Dec. 2, 1997.

Inouye et al., "The Use of Renilla Luciferase, Oplophorus Luciferase, and Apoaequorin as Bioluminescent Reporter Protein in the Presence of Coelenterazine Analogues as Substrate," *Biochemical and Biophysical Research Communications*, 233(2): 349-353 (Apr. 17, 1997).

Inouye, "Blue Fluorescent Protein from the Calcium-Sensitive Photoprotein Aequorin is a Heat Resistant Enzyme, Catalyzing the Oxidation of Coelenterazine," *FEBS Letters*, 577(1-2):105-110 (2004).

Inouye, et al. "Blue Fluorescent Protein from the Calcium-Sensitive Photoprotein Aequorin: Catalytic Properties for the Oxidation of Coelenterazine as an Oxygenase," *FEBS Letters*, 580: 1977-1982 (2006).

The Patent Office Patents Directorate, Search Report for Application No. GB0608514.6, dated Aug. 18, 2006.

Deng et al., "Crystal Structure of a Ca2+-discharged Photoprotein," *J. Biological Chemistry*, 279 (32): 33647-33652 (Aug. 6, 2004).

Inouye, "Fusions to Imidazopyrazinone-Type Luciferases and Aequorin as Reporters," *Methods in Enzymology*, 326: 165-174 (2000).

Shimomura et al., "The relative rate of aequorin regeneration from apoaequorin and coelenterazine analogues," *Biochem J.*, 296: 549-551 (1993).

Shimomura et al., "Recombinant aequorin and recombinant semi-synthetic aequorins," *Biochem J.*, 270: 309-312 (1990).

Shimomura et al., "Light-emitting properties of recombinant semi-synthetic aequorins and recombinant fluorescein-conjugated aequorin for measuring cellular calcium," *Cell Calcium*, 14: 373-378 (1993).

Vysotski et al., "Ca2+-Regulated Photoproteins: Structural Insight into the Bioluminescence Mechanism," *Acc. Chem. Res.*, 37 (6): 405-415 (2004).

Tsuji et al. "Bioluminescence Reaction Catalyzed by Membrane-Bound Luciferase in the 'Firefly Squid,' *Watasenia scintillans*," *Biochimica et Biophsica Acta* 1564: 189-197 (2002).

Shimomura, O. et al., Biochem. Biophys. Res. Commun., 53, 490-494 (1973).

Izutsu, K.T. et al., Biochem. Biophys. Res. Commun., 49, 1034-1039 (1972).

Reasons of Rejection in counterpart Japanese Application No. JP 2005-133743, mailed Jan. 26, 2010.

\* cited by examiner

SEQUENCE LISTING

<160> NUMBER OF SEQ ID NOS: 4

<210> SEQ ID NO 1
<211> LENGTH: 189
<212> TYPE: PRT
<213> ORGANISM: Aequorea aequorea

<400> SEQUENCE: 1

Val Lys Leu Thr Ser Asp Phe Asp Asn Pro Arg Trp Ile Gly Arg His
1               5                   10                  15

Lys His Met Phe Asn Phe Leu Asp Val Asn His Asn Gly Lys Ile Ser

```
                20                  25                  30
Leu Asp Glu Met Val Tyr Lys Ala Ser Asp Ile Val Ile Asn Asn Leu
            35                  40                  45

Gly Ala Thr Pro Glu Gln Ala Lys Arg His Lys Asp Ala Val Glu Ala
        50                  55                  60

Phe Phe Gly Gly Ala Gly Met Lys Tyr Gly Val Glu Thr Asp Trp Pro
65                  70                  75                  80

Ala Tyr Ile Glu Gly Trp Lys Lys Leu Ala Thr Asp Glu Leu Glu Lys
                85                  90                  95

Tyr Ala Lys Asn Glu Pro Thr Leu Ile Arg Ile Trp Gly Asp Ala Leu
            100                 105                 110

Phe Asp Ile Val Asp Lys Asp Gln Asn Gly Ala Ile Thr Leu Asp Glu
        115                 120                 125

Trp Lys Ala Tyr Thr Lys Ala Ala Gly Ile Ile Gln Ser Ser Glu Asp
    130                 135                 140

Cys Glu Glu Thr Phe Arg Val Cys Asp Ile Asp Glu Ser Gly Gln Leu
145                 150                 155                 160

Asp Val Asp Glu Met Thr Arg Gln His Leu Gly Phe Trp Tyr Thr Met
                165                 170                 175

Asp Pro Ala Cys Glu Lys Leu Tyr Gly Gly Ala Val Pro
            180                 185
```

```
<210> SEQ ID NO 2
<211> LENGTH: 198
<212> TYPE: PRT
<213> ORGANISM: Clytia gregarium

<400> SEQUENCE: 2

Met Ala Asp Thr Ala Ser Lys Tyr Ala Val Lys Leu Arg Pro Asn Phe
1               5                   10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
        35                  40                  45

Ala Ser Asp Asp Ile Cys Ala Lys Leu Gly Ala Thr Pro Glu Gln Thr
    50                  55                  60

Lys Arg His Gln Asp Ala Val Glu Ala Phe Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Gly Arg Ile
    130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185                 190

Tyr Gly Asn Phe Val Pro
            195
```

<210> SEQ ID NO 3
<211> LENGTH: 195
<212> TYPE: PRT
<213> ORGANISM: Obelia longissima

<400> SEQUENCE: 3

Met Ser Ser Lys Tyr Ala Val Lys Leu Lys Thr Asp Phe Asp Asn Pro
1               5                   10                  15

Arg Trp Ile Lys Arg His Lys His Met Phe Asp Phe Leu Asp Ile Asn
            20                  25                  30

Gly Asn Gly Lys Ile Thr Leu Asp Glu Ile Val Ser Lys Ala Ser Asp
        35                  40                  45

Asp Ile Cys Ala Lys Leu Glu Ala Thr Pro Glu Gln Thr Lys Arg His
    50                  55                  60

Gln Val Cys Val Glu Ala Phe Phe Arg Gly Cys Gly Met Glu Tyr Gly
65                  70                  75                  80

Lys Glu Ile Ala Phe Pro Gln Phe Leu Asp Gly Trp Lys Gln Leu Ala
                85                  90                  95

Thr Ser Glu Leu Lys Lys Trp Ala Arg Asn Glu Pro Thr Leu Ile Arg
            100                 105                 110

Glu Trp Gly Asp Ala Val Phe Asp Ile Phe Asp Lys Asp Gly Ser Gly
        115                 120                 125

Thr Ile Thr Leu Asp Glu Trp Lys Ala Tyr Gly Lys Ile Ser Gly Ile
    130                 135                 140

Ser Pro Ser Gln Glu Asp Cys Glu Ala Thr Phe Arg His Cys Asp Leu
145                 150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
            180                 185                 190

Gly Val Pro
        195

<210> SEQ ID NO 4
<211> LENGTH: 198
<212> TYPE: PRT
<213> ORGANISM: Mitrocoma cellularia

<400> SEQUENCE: 4

Met Ser Met Gly Ser Arg Tyr Ala Val Lys Leu Thr Thr Asp Phe Asp
1               5                   10                  15

Asn Pro Lys Trp Ile Ala Arg His Lys His Met Phe Asn Phe Leu Asp
            20                  25                  30

Ile Asn Ser Asn Gly Gln Ile Asn Leu Asn Glu Met Val His Lys Ala
        35                  40                  45

Ser Asn Ile Ile Cys Lys Lys Leu Gly Ala Thr Glu Glu Gln Thr Lys
    50                  55                  60

Arg His Gln Lys Cys Val Glu Asp Phe Phe Gly Gly Ala Gly Leu Glu
65                  70                  75                  80

Tyr Asp Lys Asp Thr Thr Trp Pro Glu Tyr Ile Glu Gly Trp Lys Arg
                85                  90                  95

Leu Ala Lys Thr Glu Leu Glu Arg His Ser Lys Asn Gln Val Thr Leu
            100                 105                 110

Ile Arg Leu Trp Gly Asp Ala Leu Phe Asp Ile Ile Asp Lys Asp Arg
        115                 120                 125

```
Asn Gly Ser Val Ser Leu Asp Glu Trp Ile Gln Tyr Thr His Cys Ala
    130             135                 140
Gly Ile Gln Gln Ser Arg Gly Gln Cys Glu Ala Thr Phe Ala His Cys
145             150                 155                 160
Asp Leu Asp Gly Asp Gly Lys Leu Asp Val Asp Glu Met Thr Arg Gln
            165             170                 175
His Leu Gly Phe Trp Tyr Ser Val Asp Pro Thr Cys Glu Gly Leu Tyr
        180             185                 190
Gly Gly Ala Val Pro Tyr
        195
```

METHOD FOR EXTENDING LIGHT-EMITTING TIME OF CALCIUM-BINDING PHOTOPROTEIN SOLUTION

TECHNICAL FIELD

The present invention relates to methods for extending light-emitting time of calcium-binding photoprotein solution that instantaneously emits light by binding to calcium ions.

DESCRIPTION OF THE RELATED ART

Calcium ion-binding photoproteins instantaneously emit light by reacting specifically with calcium ions or cations that can be substituted for the calcium ions. Especially, among calcium-binding photoproteins, most detailed studies have been conducted on aequorin, a typical calcium-binding photoprotein, which is widely used for detection of a trace amount of calcium ions. Aequorin is present as a complex composed of the apoprotein apoaequorin, the luminescent substrate coelenterazine, and oxygen (coelenterazine peroxide). When calcium ions bind to aequorin molecules, a blue light (maximum wave length: 460 nm) emission takes place instantaneously; and coelenteramide, an oxide of a coelenterazine, and carbon dioxide are released. It is known that the luminous wavelengths of other calcium ion-binding photoproteins are 470 to 490 nm due to the effect of amino acid residues contributing to stabilization of excited coelenteramide. Like aequorin, they generate coelenteramide and carbon dioxide after emitting light, indicating that they have the same luminescence mechanism as aequorin.

By analyzing the gene encoding apoaequorin, the apoprotein of aequorin, it was reported that apoaequorin is composed of 189 amino acids, has a homologous sequence with the calcium-binding protein calmodulin, and has three E-F hand motifs that have helix-loop-helix structure for calcium binding (Inouye et al. (1985), Proc. Natl. Acad. Sci. USA 82, 3154-3158). Meanwhile, it has also been confirmed by X-ray crystallographic analysis that apoaequorin has three E-F hand structures that can bind calcium. In addition, it was suggested that the 184th tyrosine residue near the C-terminus is involved in stabilization of coelenterazine peroxide; it was inferred that binding of a calcium ion to an EF hand makes peroxide unstable, triggering light emission (Head, J. F., Inouye, S., Teranishi, K. and Shimomura, O. (2000) Nature, 405, 372-376).

Another calcium-binding photoprotein obelin is about 75% homologous with aequorin in primary structure. The results of X-ray crystallographic analysis using recombinant obelin have revealed that aequorin and obelin have almost the same higher-order structure and that the type of the amino acid residue involved in stabilization of peroxide of coelenterazine serving as emission source is tyrosine in both of the proteins. (Deng, L., Vysotski, E. S., Liu, Z.-J., Markova, S. V., Malikova, N. P., Lee, J., Rose, J. and Wang, B.-C. (2001) FEBS Lett. 506, 281-285).

These photoproteins are highly sensitive to calcium ions; regarding their luminous sensitivity, as low as 1 picogram or less of calcium ions can be detected. These photoproteins have therefore been used for detection and quantification of trace calcium ions and as imaging probes for visualization of dynamic changes in intracellular calcium ions. Luminescence of calcium-binding photoproteins has advantages that the background signal that causes a problem in ordinary chemiluminescence is virtually absent since calcium-binding photoproteins emit light by specific binding to calcium ions; and that a signal with a favorable signal/noise (S/N) ratio can be rapidly obtained since their luminescent reaction itself is instantaneous, going to completion within a few seconds.

However, since, by just coming in contact with a subtle quantity of calcium ions ($10^{-7}$ mole/liter or more), calcium-binding photoproteins instantaneously emit light and the emission quenches, it has previously been impossible to maintain light emission as long as 1 minute. For example, when 1 nanogram of aequorin comes in contact with calcium ions, its light emission quenches within 10 seconds. Accordingly, when a calcium-binding photoprotein alone is used, it instantaneously emits light but cannot keep emitting light for a long time. Thus, for extending light-emitting time of calcium-binding photoproteins alone, methods of increasing the viscosity of calcium-binding photoprotein solution have been developed. For increasing the viscosity, the method (Japanese Patent Application No. 2002-193898) of increasing the concentration of calcium-binding photoprotein in the solution and the method (Japanese Patent Application No. 2003-205403) of increasing the viscosity of the solvent have been proposed.

SUMMARY OF THE INVENTION

The present invention is directed to provide new methods for extending light-emitting time of calcium-binding photoprotein solution that instantaneously emits light.

The present invention encompasses the following:

A method for extending light-emitting time of a solution of a calcium-binding photoprotein emit light using a calcium ion or another cation that can be substituted for the calcium ion, including performing a light-emitting reaction in the presence of an anion capable of binding to the calcium ion or the other cation that can be substituted for the calcium ion.

A method for extending light-emitting time of a solution of a calcium-binding photoprotein emit light using a calcium ion or another cation that can be substituted for the calcium ion, including performing a light-emitting reaction in the presence of a cation that can bind to the calcium-binding site of the calcium-binding photoprotein with a lower affinity than the calcium ion or another cation that can be substituted for the calcium ion without activating the calcium-binding photoprotein.

A method for extending light-emitting time of a solution of a calcium-biding photoprotein emit light using a calcium ion or another cation that can be substituted for the calcium ion, including performing a light-emitting reaction in the presence of both an anion capable of binding to the calcium ion or the cation that can be substituted for the calcium ion and a cation that can bind to the calcium-binding site of the calcium-binding photoprotein with a lower affinity than the calcium ion or another cation that can be substituted for the calcium ion without activating the calcium-binding photoprotein.

In an aspect of the method according to this invention, the anion is a sulfate ion.

In another aspect of the method according to this invention, the cation that can bind to the calcium-binding site of the calcium-binding photoprotein without activating the calcium-binding photoprotein is a magnesium ion or a zinc ion.

In another aspect of the method according to this invention, the cation that can be substituted for the calcium ion is a strontium ion or a cadmium ion.

In another aspect of the method according to this invention, the calcium-binding photoprotein is a protein composed of an apoprotein and a peroxide of a coelenterazine or an analog thereof.

In another aspect of the method according to this invention, the coelenterazine or the analog thereof is represented in the following formula (1) or (2):

(1)

(2)

wherein $R^1$ is a substituted or unsubstituted aryl group, a substituted or unsubstituted arylated alkyl group, or a straight or branched chain alkyl group that may be substituted for an aliphatic cyclic group;

$R^2$ is a substituted or unsubstituted aryl group, a substituted or unsubstituted arylated alkyl group, a substituted or unsubstituted aryl alkenyl group, a straight or branched chain alkyl group that may be substituted for an aliphatic cyclic group, a straight or branched chain alkenyl group that may be substituted for an aliphatic cyclic group, or a heterocyclic group;

$R^3$ is a hydrogen atom, or a substituted or unsubstituted alkyl group;

$X^1$ is a hydrogen atom, a hydroxyl group, a halogen atom, an alkoxyl group, or an amino group;

$X^2$ is a hydrogen atom or a hydroxyl group; and

Y is a divalent hydrocarbon group having 1 to 4 carbon atoms.

In another aspect of the method according to this invention, in the formula (1) or formula (2), $R^1$ is an unsubstituted aryl group, an unsubstituted arylated alkyl group, an arylated alkyl group substituted for a hydroxyl group or a halogen atom, or a straight or branched chain alkyl group that may be substituted for a cyclohexyl group;

$R^2$ is an unsubstituted aryl group, an aryl group substituted for a hydroxyl group, an unsubstituted arylated alkyl group, an arylated alkyl group substituted for a hydroxyl group, an unsubstituted aryl alkenyl group, an unsubstituted straight or branched chain alkyl group, a straight chain alkyl group that may be substituted for an aliphatic cyclic group, a branched chain alkenyl group, or a heterocyclic group containing sulfur;

$R^3$ is a hydrogen atom, a methyl group, or 2-hydroxyethyl group;

$X^1$ is a hydrogen atom, a hydroxyl group, a fluorine atom, a methoxy group, or an amino group; and Y is a methylene group, ethylene group, a propylene group, or a vinylene group.

In another aspect of the method according to this invention, in the formula (1) or (2), $R^1$ is a phenyl group, a benzyl group, a p-hydroxybenzyl group, a p-fluorobenzyl group, a p-chlorobenzyl group, a p-bromobenzyl group, a p-iodinebenzyl group, a 3, 4-difluorobenzyl group, a pentafluorobenzyl group, a phenylethyl group, a phenylpropyl group, a naphthylmethyl group, a cyclohexylmethyl group, a methyl group, a 1-methylpropyl group, or a 2-methylpropyl group;

and $R^2$ is a phenyl group, a p-hydroxy phenyl group, a benzyl group, an α-hydroxybenzyl group, a phenylethyl group, a phenylvinyl group, a cyclohexyl group, a cyclohexylmethyl group, a cyclohexylethyl group, a methyl group, an ethyl group, a propyl group, a 2-methylpropyl group, a 2-methylpropenyl group, an adamantylmethyl group, a cyclopentylmethyl group, or a thiophene-2-yl group.

In another aspect of the method according to this invention, in a molecule of the calcium-binding photoprotein, the ratio of the number of molecules of the apoprotein to the number of molecules of the peroxide of the coelenterazine or the analog thereof is 1:1.

In another aspect of the method according to this invention, the apoprotein is an apoprotein having the amino acid sequence shown in any one of SEQ ID NOs: 1 to 4 or a mutant apoprotein in which one or more amino acids are deleted, substituted, or added in the sequences shown in SEQ ID NOs: 1 to 4.

In another aspect of the method according to this invention, wherein the calcium-binding photoprotein is a protein selected from the group consisting of aequorin, clytin, obelin, mitrocomin, mineopsin, and bervoin.

A kit for extending light-emitting time in making a solution of a calcium-binding photoprotein emit light using a calcium ion or a cation that can be substituted for the calcium ion, including:

a first solution containing the calcium ion or the cation that can be substituted for the calcium ion;

and at least one of a second solution containing an anion capable of binding to the calcium ion or the cation that can be substituted for the calcium ion and a third solution containing a cation that can bind to the calcium-binding site of the calcium-binding photoprotein with a lower affinity than the calcium ion or the cation that can be substituted for the calcium ion without activating the calcium-binding photoprotein.

In an aspect of the kit according to this invention, the anion is a sulfate ion.

In another aspect of the kit according to this invention, the cation that can bind to the calcium-binding site of the calcium-binding photoprotein without activating the calcium-binding photoprotein is a magnesium ion, or a zinc ion.

In another aspect of the kit according to this invention, the cation that can be substituted for the calcium ion is a strontium ion or a cadmium ion.

In another aspect of the kit according to this invention, the calcium-binding photoprotein is a protein selected from the group consisting of aequorin, clytin, obelin, mitrocomin, mineopsin, and bervoin.

A "calcium-binding photoprotein" refers to a protein that reacts with calcium ions or cations that can be substituted for the calcium ions and emits light. The examples include aequorin, clytin, obelin, mitrocomin, mineopsin, and bervoin.

These calcium-binding photoproteins are composed of an apoprotein and peroxide of coelenterazine or its analog.

Table 1 lists the apoproteins whose gene has been isolated to date.

TABLE 1

| Name of photoprotein | Scientific name | Japanese name/ Common name | GeneBank Acc. No. | Authors (year) |
|---|---|---|---|---|
| Aequorin | Aequorea victoria | Owankurage | AEVAQ440X: L29571 | Inouye et al. (1985) |
| Aequorin | Aequorea victoria | Owankurage | — | Charbonnueau et al. (1985) |
| Aequorin | Aequorea victoria | Owankurage | AEVAEQA: M16103 | Prasher et al. (1987) |
| Aequorin | Aequorea parva | Owankurage | AY013822 | Luo et al. (2000) |
| Aequorin | Aequorea macrodactyla | Hitomoshikurage | AY013823 | Luo et al. (2000) |
| Clytin | Clytiagregarium | Kozarakurage | CY1APOCLYT: L13247 | Inouye & Tsuji (1993) |
| Mitrocomin | Mitrocoma cellularia | | MITMI17: L31623 | Fagan et al. (1993) |
| Obelin | Obelia longissima | Oberiakurage | OLU07128: U07128 | Illarionov et al. (1995) |
| Obelin | Obelia geniculata | Oberiakurage | AF394688 | Markova et al. (2002) |

DESCRIPTION OF THE PREFERRED EMBODIMENT

The present invention provides methods for extending light-emitting time when making calcium-binding photoprotein solution emit light using calcium ions or cations that can be substituted for the calcium ions.

Unless otherwise explained, methods described in standard sets of protocols such as J. Sambrook and E. F. Fritsch & T. Maniatis (Ed.), "Molecular Cloning, a Laboratory Manual (3rd edition), Cold Spring Harbor Press and Cold Spring Harbor, N.Y. (2001); and F. M. Ausubel, R. Brent, R. E. Kingston, D. D. Moore, J. G. Seidman, J. A. Smith, and K. Struhl (Ed.), "Current Protocols in Molecular Biology," John Wiley & Sons Ltd., or their modified/refined methods are used. When using commercial reagent kits and measuring apparatus, unless otherwise explained, protocols attached to them are used.

The objective, characteristics, and advantages of the present invention as well as the idea thereof are apparent to those skilled in the art from the descriptions given herein. It is to be understood that the embodiments and specific examples of the invention described hereinbelow are to be taken as preferred examples of the present invention. These descriptions are only for illustrative and explanatory purposes and are not intended to restrict the invention to these embodiments or examples. It is further apparent to those skilled in the art that various refinements and modifications may be made based on the descriptions given herein within the intent and scope of the present invention disclosed herein.
(1) Apoprotein that Constitutes a Calcium-Binding Photoprotein The homology of the amino acid sequences of these apoproteins is 60% or higher, and all of these apoproteins can be regenerated to calcium-binding photoproteins from the luminescent substrate coelenterazine. Further, recent x-ray crystal analysis of aequorin and obelin, both of which are photoproteins, has revealed that the backbone structures of their higher-order structures are almost the same. From this, homology of the higher-order structures of other calcium-binding photoproteins can easily be inferred by analogy. Thus, although aequorin, a typical calcium-binding photoprotein, was used in Examples herein, the results obtained can be obviously applicable to other calcium-binding photoproteins.

Aequorin can be regenerated from apoaequorin, the luminescent substrate coelenterazine, and oxygen, as mentioned above. Here, by using a coelenterazine analog in place of coelenterazine, a novel photoprotein referred to as a semi-synthesized aequorin with different luminous wavelengths and calcium-binding ability can be created. Other calcium-binding photoproteins can also be used to create a novel photoprotein. The results of X-ray crystallographic analyses of semi-synthesized aequorin have shown that its basic structure is also almost the same as that of aequorin.

The amino acid sequence of the apoaequorin that is the apoprotein of natural aequorin is shown in SEQ ID NO: 1. Besides the apoaequorin having amino acid sequence described in SEQ ID NO: 1, any apoaequorin mutant can be used whether it may be known or unknown as long as it is capable of constituting a calcium-binding photoprotein. The apoaequorin used in the present invention thus includes the apoaequorin having the amino acid sequence described in SEQ ID NO: 1 as well as mutant apoaequorins in which one or more amino acids are deleted, substituted, or added in the amino acid sequence described in SEQ ID NO: 1. One example of a particularly preferred mutant apoaequorin is the mutant in which the first Val is substituted for Ala-Asn-Ser in SEQ ID NO: 1.

The amino acid sequence of the apoclytin that is the apoprotein of the wild-type clytin, is shown in SEQ ID NO: 2. The amino acid sequence of the apoobelin that is the apoprotein of the wild-type obelin, is shown in SEQ ID NO: 3. The amino acid sequence of the apomitrocomin that is the apoprotein of the wild-type mitrocomin, is shown in SEQ ID NO: 4. These may be mutants in which one or more amino acids are deleted, substituted, or added in each of the sequences.

These apoproteins may be either prepared from the nature or produced by genetic engineering. In addition, the amino acid sequence of the calcium-binding photoprotein may be mutated by gene recombination technology, as long as it has the aforementioned luminescence activity.

(2) Method for Emitting Light of Calcium-Binding Photoprotein Solution

In this invention, the preferred cations that can be substituted for calcium ions are divalent or trivalent cations. Examples of such cations include cadmium ions, strontium ions, or lead ions. Cations are not limited to any specific ones as long as they bind to and activate a calcium-binding photoprotein, thereby making it emit light.

The solvent used for calcium-binding photoprotein solution is not limited to any specific one as long as it is a fluid in which a calcium-binding photoprotein can emit light. It may be, for example, an artificial fluid, a natural fluid, or a body fluid. To make extension of light-emitting time much longer, the viscosity of the solvent may be increased by adding a water-absorbing polymer gel composition (Japanese Patent Application No. 2003-205403). Examples of the water-absorbing polymer gel compositions include, for example, starches, celluloses, and synthetic polymers, any of which can be used. Synthetic polymers include polyacrylates, polyvinyl alcohols, polyacrylamides, and polyoxyethylenes, any of which can be used.

Although preferred concentrations of a calcium-binding photoprotein in a solution are 0.1 to 10 mg/ml, emission time can be extended much longer by increasing the concentration to 10 to 500 mg/ml (Japanese Patent Application No. 2002-193898). When calcium ions or cations that can be substituted for the calcium ions are added to a solution of these calcium-binding photoprotein, the calcium-binding photoprotein is instantanesouly activated, reacts with the calcium ions or cations that can be substituted for the calcium ions, and the conformation of the apoprotein changes all at once. Then, peroxide of coelenterazine or its analog is oxidized and released as coelenteramide or its analog. In this reaction, the calcium-binding photoprotein instantaneously emits light and the emission quenches by just adding a subtle quantity of calcium ions ($10^{-7}$ mole/liter or more) to the solution. For example, when 1 nanogram of aequorin comes in contact with calcium ions, light emission of the solution is completed within 10 seconds.

Light emission time can be extended by performing the above-mentioned light-emitting reaction in the presence of anions capable of binding to the calcium ions or cations that can be substituted for the calcium ions and/or cations that can bind to the calcium-binding site of the calcium-binding photoprotein with a lower affinity than the calcium ions or the cations that can be substituted for the calcium ions without activating the calcium-binding photoprotein. Under optimal conditions, the emission time can be extended to 6 hours.

The anions capable of binding to the calcium ions or cations that can be substituted for the calcium ions are not limited to any specific ones as long as emission time can be extended when the anions (e.g., sulfate ions and carbonate ions) are added to the solution in which a light-emitting reaction is performed. Preferred ion concentrations are 0.6 to 1.5M, but are not particularly limited to this range. These anions inhibit calcium ions or cations that can be substituted for the calcium ions from approaching to the calcium-binding photoprotein by binding to the calcium ions or cations. This makes the calcium ions or cations collide less frequently with the calcium-binding photoprotein in the reaction mixture, so that the calcium ions or cations collide gradually with the photoprotein over a long time. As a result, the solution as a whole emits light for a long time, making emission time extend longer than under ordinary conditions.

Further, cations that can bind to the calcium-binding site of the calcium-binding photoprotein with a lower affinity than the calcium ions or the cations that can be substituted for the calcium ions and without activating the calcium-binding photoprotein include magnesium ions, and zinc ions but are not limited to any specific ones as long as they are satisfied with the above-mentioned conditions. These cations, when present with calcium ions or cations that can be substituted for the calcium ions, competitively bind to the calcium-binding site of a calcium-binding photoprotein but do not react with the calcium-binding photoprotein. Accordingly, the proportion of calcium ions or cations that can be substituted for the calcium ions which bind to the calcium-binding site of the photoprotein decreases, thereby causing the photoprotein in the solution to react gradually. As a result, the solution as a whole emit light for a long time and light-emitting time is extended longer than under ordinary conditions. However, for the reaction mixture to keep emitting light, these cations must be exchanged with calcium ions or cations that can be substituted for the cations which have bound to the calcium-binding site of the photoprotein before being. For this reason, these cations must have a lower affinity with the calcium-binding site of a photoprotein than calcium ions or cation that can be substituted for the calcium ions.

EXAMPLE

The present invention is explained in the following examples, but these examples are not to be construed to limit the present invention.

(1) Preparation of Recombinant Aequorin

As shown below, recombinant aequorins were obtained by expressing the recombinant apoaequorin gene in the *E. coli* described in Japanese Laid-Open Application No. 1989-132397, regenerating recombinant aequorins by binding the expressed product to coelenterazine, and then purifying the complexes as described in Japanese Laid Open Application No. 2001-270899. The recombinant apoaequorins thus obtained are composed of 191 amino acids, whose N-terminus starts from Ala-Asn-Ser-(Val- of the N-terminus of SEQ ID NO: 1 was replaced by Ala-Asn-Ser-).

(1-1) Expression of Recombinant Apoaequorins in *E. coli*

First, to express recombinant apoaequorins in *E. coli*, the apoaequorin gene expression vector piP-HE (refer to Japanese Laid-Open Application No. 1989-132397) constructed from pAQ440 harboring the apoaequorin gene (refer to Japanese Laid-Open Application No. 1986-135586) was used. *E. coli* strain WA802 was used as the host and was transformed with piP-HE using the conventional methods. The transformant obtained was incubated at 30° C. overnight, inoculated into 50 ml of LB liquid medium (bactotrypton 1% w/v, yeast extract 0.5% w/v, sodium chloride 0.5% w/v, pH 7.2 in water) containing ampicillin (50 µg/ml), and further incubated at 30° C. for 8 hours. Then, the culture was added to a fresh LB liquid media and incubated at 37° C. at for a day and night (18 hours). After incubation, the resulting culture was separated into bacterial cells and medium by low-speed centrifugation (5,000×g). Since both the bacterial cells and the medium contain expressed recombinant apoaequorins, they were stored separately as the starting material for aequorin purification.

The harvested bacterial cells were suspended in 400 ml buffer (50 mM Tris-HCl, pH 7.6, 10 mM EDTA) containing 200 mg of a reducing agent dithiothreitol (DTT, manufactured by Wako Pure Chemicals Industries, Ltd.). The cells were crushed by treating with an ultrasonicator for 2 min under on ice, and centrifuged at 12,000×g for 20 min. Then, the supernatant was recovered. Chemosynthesized coelenterazine was dissolved in a small quantity of methanol, added to the supernatant obtained at 1.2-fold molar concentration of apoaequorin to be produced, and allowed to stand at 4° C. for 5 hours or longer. This supernatant was immediately loaded onto a Q-Sepharose column (Amersham Pharmacia Biotech, 2×10 cm diameter) pre-equilibrated with a buffer of 20 mM Tris-HCl, pH 7.6, 10 mM EDTA, to have aequorin adsorbed. The column was washed with a buffer of 20 mM Tris-HCl, pH 7.6, 10 mM EDTA, 0.1 M NaCl until the absorbance of the wash flowing out from the column at 280 nm becomes 0.05 or less. Then, the apoaequorin and aequorin adsorbed on the column were eluted with a linear concentration gradient of 0.1 to 0.4 M NaCl.

(1-2) Isolation of Aequorin that has Formed Complexes

Aequorin that has formed complexes with coelenterazine was isolated from apoaequorin that has not formed complexes, using a hydrophobic chromatography with Butyl Sparse 4 Fast Flow gel. That is, the orange eluent from the Q-Sepharose column was adjusted at final ammonium sulfate concentration at 2 M, and then the precipitant was removed by centrifugation. The supernatant was applied to a Butyl Sepharose 4 Fast Flow column (Amersham Pharmacia Biotech, column size: 2×10 cm diameter) pre-equilibrated with 20 mM Tris-HCl, pH 7.6, 10 mM EDTA, containing 2 M ammonium sulfate, and the orange regenerated aequorin fractions having chemiluminescence activity were eluted by a linear concentration gradient to a final ammonium sulfate concentration at 1 M and recovered.

The unregenerated apoaequorin was eluted only with 20 mM Tris-HCl, pH 7.6, 10 mM EDTA. The regenerated aequorin fractions were analyzed by SDS-PAGE using 12% polyacrylamide gel under a reducing condition. As a result, a single band with a molecular weight equivalent to that of a 25 kDa protein was detected in the purified fraction, with a purity of 98% or higher according to densitometer measurement.

The recovery rate of aequorin from the bacterial cells was about 80%. A total of 80 mg of high-purity aequorin was thus obtained.

(1-3) Purification of Aequorin from Culture Media

Meanwhile, high-purity aequorin was purified from the culture medium according to the method described in Japanese Laid-Open Application No. 1989-132397. That is, the culture medium was subjected to acidification treatment to pH 5 or below and allowed to stand at 4° C. for 60 min or longer. The white-precipitated apoaequorin was isolated by centrifugation and dissolved in the above-mentioned buffer (50 mM Tris-HCl, pH 7.6, 10 mM EDTA) containing a reducing agent. Then, after regenerating to aequorin in the same manner as in purification method from bacterial cells, aequorin with a purity of 98% or higher was obtained by the sepharose column chromatography and the Butyl Sepharose 4 Fast Flow column chromatography. The resulting purified aequorin was analyzed by SDS-PAGE using 12% polyacrylamide gel under a reducing condition. As a result, a single band with a molecular weight equivalent to that of a 25 kDa protein was detected with a purity of 98% or higher according to densitometer measurement. A total of 45 mg of high-purity aequorin was obtained from 50 mg of apoaequorin obtained from the culture medium. The amount of proteins was determined using a commercially available kit (manufactured by Bio-Rad Laboratories, Inc.) based on the Bradford method. Bovine serum albumin (manufactured by Pierce Laboratories Inc.) was used as the standard substance.

(2) Preparation of a Semi-Synthesized Aequorin

Semi-synthesized aequorin was prepared according to the methods described in Japanese Laid-Open Application No. 1989-132397. First, high-purity apoaequorin (10 mg) was dissolved in 20 mM Tris-HCl, pH 7.6, 10 mM EDTA, and chemosynthesized coelenterazine analog dissolved in a small quantity of methanol was added at 1.2-fold molar concentration of apoaequorin. The mixture was allowed to stand at 4° C. for 5 hours or longer to regenerate into semi-synthesized aequorin. This solution was adjusted to a final ammonium sulfate concentration of 2M, applied to a Butyl Sepharose 4 Fast Flow column (Amersham Pharmacia Biotech, column size: 2×8 cm diameter) pre-equilibrated with 20 mM Tris-HCl, pH 7.6, 10 mM EDTA, containing 2 M ammonium sulfate, eluted by a linear concentration gradient to a final ammonium sulfate concentration at 1 M. Thus, orange aequorin fractions having chemiluminescence activity were obtained.

(3) Method for Extending Period of Light Emission of the Calcium-Binding Photoprotein Aequorin by Addition of Calcium in the Presence of Various Salts The salts shown in Table 2 were added to a buffer of 10 mM Tris-HCl, pH 7.6, 0.1 mM EDTA at a final salt concentration of 0.6 M or 1.2 M. 1.0 μg of the calcium-binding photoprotein aequorin was added to this solution (100 μl) containing each salt. After further addition of a buffer (100 μl) of 10 mM Tris-HCl, pH 7.6, 0.1 mM EDTA, containing 1 mM calcium chloride and 0.6 M or 1.2 M salt, the mixture was stirred. Then, luminescence activity was measured with the luminometer Luminescencer-PSN AB2200 (manufactured by Atto Co., Ltd.) for 600 seconds. Table 3 shows half-lives (the time taken to fall to 50% of the maximum activity: $T_{1/2}$) of luminescence intensity of aequorin produced by calcium ions in the presence of various salts as well as their maximum luminescence intensities.

TABLE 2

| Compound | Name of distributor | Product number |
| --- | --- | --- |
| Ammonium sulfate | Wako Pure Chemical Industries, Ltd. | 019-03435 |
| Magnesium sulfate | Wako Pure Chemical Industries, Ltd. | 131-00405 |
| Zinc sulfate | Wako Pure Chemical Industries, Ltd. | 268-00405 |
| Potassium sulfate | Kokusan Chemical Co., Ltd. | 2114381 |
| Ammonium chloride | Wako Pure Chemical Industries, Ltd. | 017-02995 |
| Magnesium chloride | Wako Pure Chemical Industries, Ltd. | 139-09203 |
| Strontium chloride | Wako Pure Chemical Industries, Ltd. | 195-07361 |
| Zinc chloride | Wako Pure Chemical Industries, Ltd. | 268-01022 |
| Ammonium bicarbonate | Wako Pure Chemical Industries, Ltd. | 017-02875 |

TABLE 3

| Salts | Final concentration of CaCl$_2$ added (mM) | T$_{1/2}$ (min) 0.6 M | T$_{1/2}$ (min) 1.2 M | Imax (rlu) 1.2 M |
|---|---|---|---|---|
| (NH$_4$)$_2$SO$_4$ | 0.5 | 0.12 | 11.83 | 15546 |
| MgSO$_4$ | 0.5 | 13.22 | 60.47 | 1061 |
| ZnSO$_4$ | 0.5 | 2.87 | 7.78 | 4065 |
| K$_2$SO$_4$ | 0.5 | 0.03 | N.D. | — |
| NH$_4$Cl | 0.5 | 0.02 | 0.02 | 63211 |
| MgCl$_2$ | 0.5 | 7.39 | 46.73 | 3944 |
| SrCl$_2$ | 0.5 | 0.08 | 0.08 | 3891 |
| ZnCl$_2$ | 0.5 | 0.18 | 0.25 | 591 |
| NH$_4$HCO$_3$ | 0.5 | 0.03 | 0.17 | 645085 |
| None | 0.5 | — | 0.02 | 130216 |

N.D.: Not dissolved
T$_{1/2}$: Half-life of luminescence intensity
Imax: Maximum luminescence intensity
rlu: Relative luminescence intensity
—: Not measured As shown in Table 3, when ammonium sulfate, magnesium sulfate, zinc sulfate, magnesium chloride, strontium chloride, zinc chloride, and sodium bicarbonate were added to the reaction system, the luminescence of aequorin was not instantaneous light emission but apparent continuous luminescence, indicating that light emission time was extended. In contrast, the other salts were shown to have no prominent effect of extending emission time of aequorin.

Whenever sulfate ions were added, extension of the light emission time was observed, suggesting that the effect of extending emission time of aequorin exerted by the addition of ammonium sulfate, magnesium sulfate, and zinc sulfate was caused by sulfate ions. The mechanism of extending emission time is inferred as follows. As the effect of high-concentration of sulfate ions, dissociative ionic bonds are formed with calcium ions, causing a competitive reaction for calcium ions between sulfate ions and apoaequorin involved in the aequorin luminescence. As a result, the binding efficiency of calcium ions to aequorin decreases, thereby causing apparent shortage of calcium ions to bind to aequorin. This makes calcium ions bind to aequorin gradually, not all at once, and, accordingly, emission time of the solution is extended as a whole.

Meanwhile, ammonium chloride does not have the effect of extending light-emitting time, suggesting that chloride ions have no effect of light extending emission time. Since magnesium chloride has the effect of extending light-emitting time, it is inferred that, here, magnesium ions are responsible for the effect of extending light-emitting time. The fact that magnesium sulfate, used in combination with sulfate ions that have the effect of extending emission time, is the most effective compound for extending light-emitting time supports that magnesium has the effect of extending light-emitting time. The mechanism of extending emission time is inferred as follows in this case. Theoretically, when a high concentration of magnesium ions is contained in the light-emitting reaction system of aequorin, magnesium ions bind to the three calcium ion-bonding sites (EF-hand motifs) in aequorin, competing with calcium ions for aequorin. This reduces the efficiency of binding between calcium ions and aequorin, thereby causing calcium to slowly bind to aequorin. As a result, light-emitting time of the solution as a whole is extended.

(4) Method for Extending Emission Time of the Calcium-Binding Photoprotein Aequorin by Addition of Cadmium in the Presence of Various Salts The final concentrations of salts shown in Table 2 were adjusted in a buffer of 10 in M Tris-HCl, pH 7.6, 0.1 mM EDTA to 0.6 or 1.2 M. 1.0 µg of the calcium-binding photoprotein aequorin was added to this solution (100 µl) containing each salt. After further addition of a buffer (100 µl) of 10 mM Tris-HCl, pH 7.6, 0.1 mM EDTA, containing 1 mM cadmium chloride and 0.6 or 1.2 M salt, the mixture was stirred. Then, Luminescence activity was measured with the luminometer Luminescencer-PSN AB2200 (manufactured by Atto Co., Ltd.) for 600 seconds. Table 4 shows the half-life values (the time required to fall to 50% of the maximum activity: T$_{1/2}$) of luminescence intensity of aequorin by calcium ions in the presence of various salts and their maximum luminescence intensities.

TABLE 4

| Salts | Final concentration of CdCl$_2$ added (mM) | T$_{1/2}$ (min) 0.6 M | T$_{1/2}$ (min) 1.2 M | Imax (rlu) 1.2 M |
|---|---|---|---|---|
| (NH$_4$)$_2$SO$_4$ | 0.5 | 0.38 | 48.96 | 9816 |
| MgSO$_4$ | 0.5 | 84.88 | 644.56 | 640 |
| ZnSO$_4$ | 0.5 | 2.33 | 3.95 | 7038 |
| MgCl$_2$ | 0.5 | 175.06 | 192.83 | 406 |
| ZnCl$_2$ | 0.5 | 0.17 | 0.13 | 1814 |
| None | 0.5 | — | 0.03 | 147127 |

T$_{1/2}$: Half-life of luminescence intensity
Imax: Maximum luminescence intensity
rlu: Relative luminescence intensity
—: Not measured As a result of comparison of the half-lives of the light emission intensities by the addition of cadmium in the presence of various salts, shown in Table 4, it was found that light-emitting time of aequorin is extended by the addition of any one of ammonium sulfate, magnesium sulfate, zinc sulfate, magnesium chloride, and zinc chloride to the reaction system. It is inferred that the cause of effect of extending emission time of aequorin is the same as that in Example 3.

(5) Method for Extending Light-Emitting Time of the Calcium-Binding Photoprotein Aequorin by Addition of Strontium in the Presence of Various Salts The final salt concentrations shown in Table 2 were adjusted in a buffer of 10 mM Tris-HCl, pH 7.6, 0.1 mM EDTA to 0.6 or 1.2 M. 1.0 µg of the calcium-binding photoprotein aequorin was added to this solution (100 µl) containing each salt. After further addition of a buffer (100 µl) of 10 mM Tris-HCl, pH 7.6, 0.1 mM EDTA containing 1 mM strontium chloride and 0.6 or 1.2 M salt, the mixture was stirred, Then, luminescence activity was measured with the luminometer Luminescencer-PSN AB2200 (manufactured by Atto Co., Ltd.) for 600 seconds. Table 5 shows the half-lives (the time required to fall to 50% of the maximum activity: T1$_{/2}$) of luminescence intensity of aequorin by calcium ions in the presence of various salts and their maximum luminescence intensities.

TABLE 5

| Salts | Final concentration of SrCl$_2$ added (mM) | T$_{1/2}$ (min) 0.6 M | T$_{1/2}$ (min) 1.2 M | Imax (rlu) 1.2 M |
|---|---|---|---|---|
| (NH$_4$)$_2$SO$_4$ | 0.5 | ppt | ppt | 14 |
| MgSO$_4$ | 0.5 | ppt | ppt | 26 |
| ZnSO$_4$ | 0.5 | 4.60 | 7.32 | 2067 |
| MgCl$_2$ | 0.5 | N.D. | N.D. | 32 |
| ZnCl$_2$ | 0.5 | 0.23 | 0.10 | 2245 |
| None | 0.5 | — | 0.03 | 1327351 |

T$_{1/2}$: Half-life of luminescence intensity
Imax: Maximum luminescence intensity
rlu: Relative luminescence intensity
—: Not measured
ppt: Strontium sulfate precipitated
N.D.: Not detectable As a result of the comparison of the half-lives of the light emission intensities by the addition of strontium in the presence of various salts, it was found that when zinc sulfate and zinc chloride are added to the reaction system, light-emitting time of aequorin is extended. In contrast, the other salts were revealed to have no marked effect of extending emission time of aequorin. The sulfate ions, which were shown to have the effect of extending light-emitting time in Examples 3 and 4, reacts with strontium and thereby become less soluble strontium sulfate, resulting in precipitation. This was considered to be the reason light-emitting reaction did not proceed in the sulfate used here. In magnesium chloride, light-emitting reaction did not proceed either. That is considered to be due to the fact that magnesium ions have higher binding ability to aequorin than strontium ions.

Figure 1:
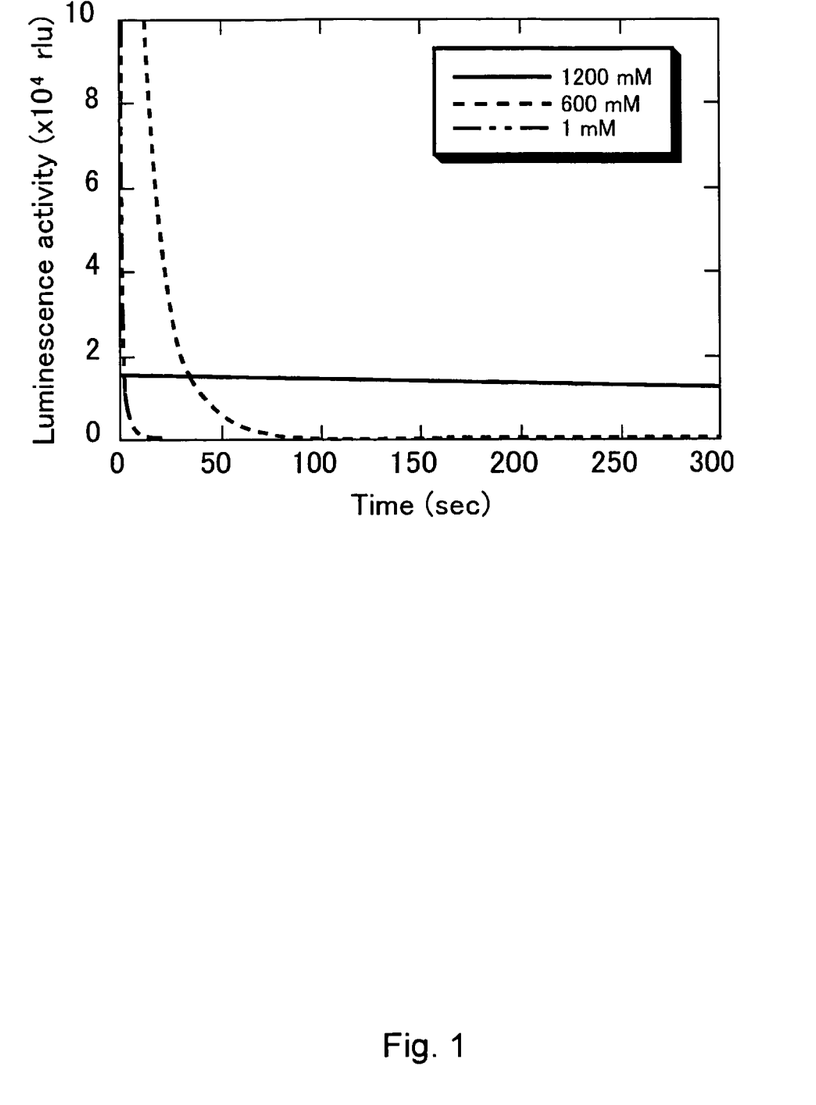
FIG. 1 shows the light-emission patterns of aequorin when ammonium sulfate is contained in the light-emitting reaction system of aequorin at 1 mM, 600 mM, and 1200 mM in an example according to the present invention.
Figure 2:
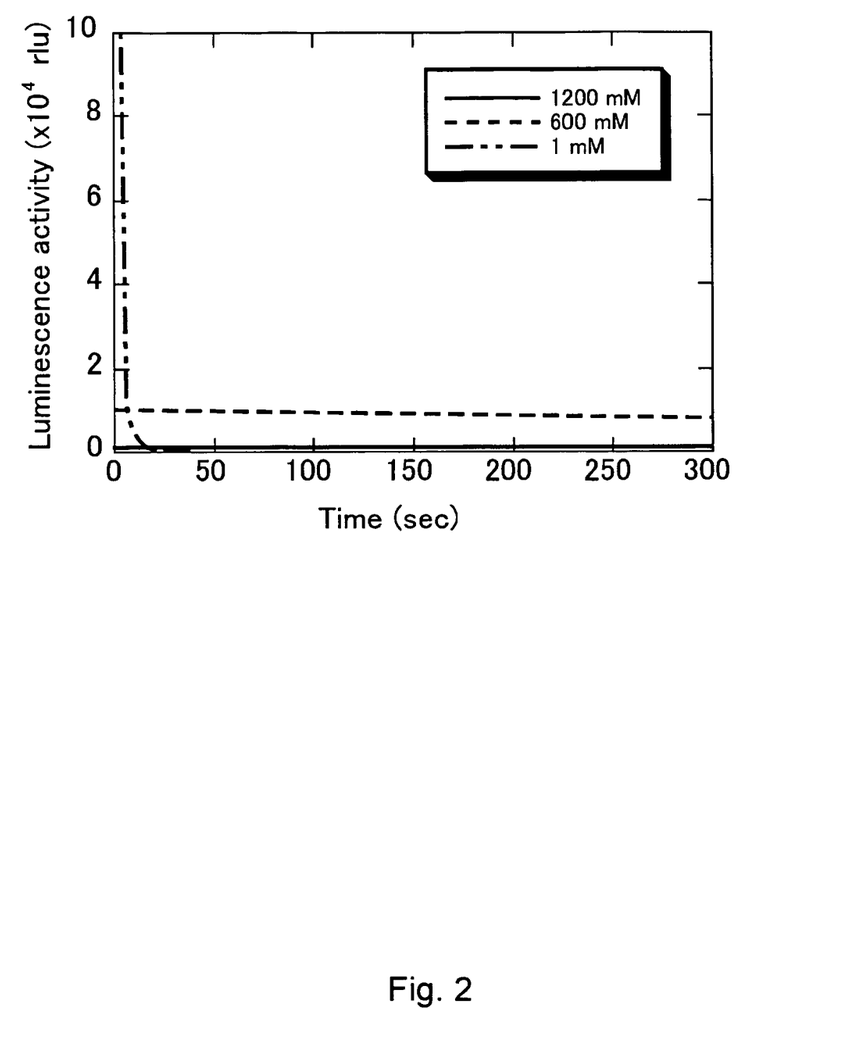
FIG. 2 shows the light-emission patterns of aequorin when magnesium sulfate is contained in the light-emitting reaction system at 1 mM, 600 mM, and 1200 mM in an example according to the present invention.
Figure 3:
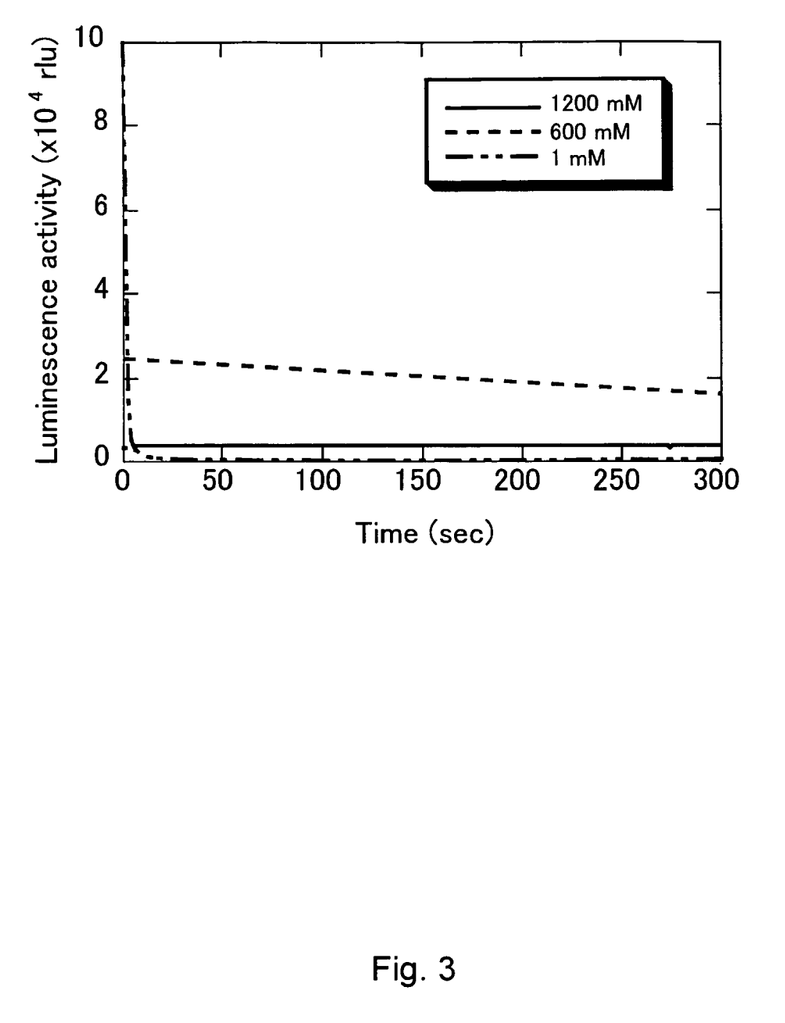
FIG. 3 shows the light-emission patterns of aequorin when magnesium chloride is contained in the light-emitting reaction system at 1 mM, 600 mM, and 1200 mM in an example according to the present invention.

(6) Determination of Optimum Concentrations of the Various Salts Exhibiting the Effect of Extending Light-Emitting Time of the Calcium-Binding Photoprotein Aequorin The effect of the concentration of ammonium sulfate, magnesium sulfate, or magnesium chloride, which exhibited a marked effect of extending light-emitting time of aequorin, was examined in detail. The final concentration of solutions containing each salt were adjusted to the followings with a buffer of 10 mM Tris-HCl, pH 7.6, 0.1 mM EDTA: 1, 10, 100, 300, 600, 1000, 1200, and 1500 mM. 1.0 µg of aequorin was added to each salt-containing solution (100 µl). After adding to each of the solutions 100 µl of a solution containing the same concentration of ammonium sulfate, magnesium sulfate, or magnesium chloride containing 1 mM calcium chloride as each solution to be added and stirring, their luminescence activity was measured with the luminometer Luminescencer-PSN AB2200 (manufactured by Atto Co., Ltd.) for 600 seconds. Table 6 shows the half-lives of luminescence intensity and maximum luminescence intensities of aequorin at various concentrations of various salts. The light emission patterns of aequorin solution when it contains ammonium sulfate, magnesium sulfate, or magnesium chloride at 1 mM, 600 mM, and 1200 mM, are shown in FIG. 1, 2, or 3, respectively.

involved in the effect of extending light-emitting time of aequorin as described above, but the results of the experiment thus revealed that in the presence of both sulfate ions and magnesium ions, the effect of extending emission time is further enhanced as compared with that in the presence of either sulfate ions or magnesium ions alone. It is therefore concluded that magnesium sulfate is the salt that extends emission time of aequorin most efficiently.

Figure 4:
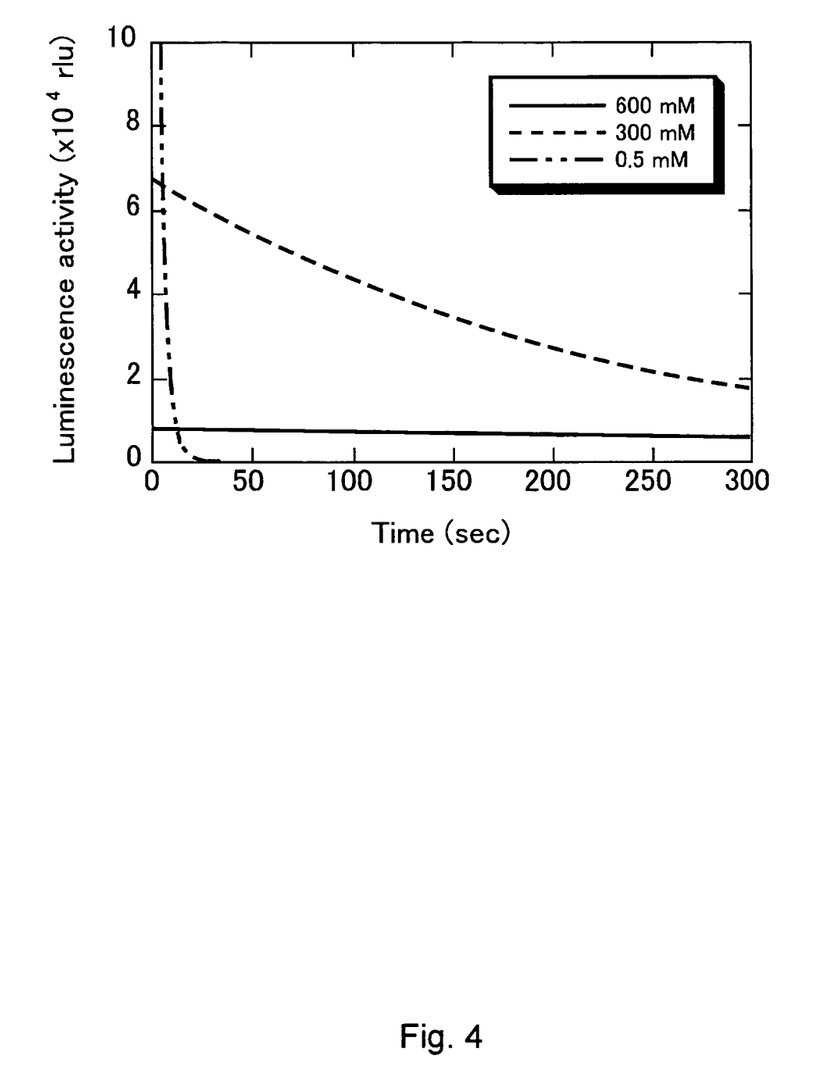
FIG. 4 shows the light-emission patterns of aequorin when ammonium sulfate at 300 mM and magnesium chloride at 0.5 mM, 300 mM, and 600 mM are contained in the light-emitting reaction system in an example according to the present invention.

(7) The Synergistic Effect of Magnesium Ions and Sulfate Ions in Light Emission of Aequorin A buffer of 10 mM Tris-HCl, pH 7.6, 0.1 mM EDTA, containing 0.6 M ammonium sulfate was prepared. 1.0 µg of aequorin was added to this solution (100 µl). After further addition of 100 µl of a buffer of 10 mM Tris-HCl, pH 7.6, 0.1 mM EDTA, containing magnesium chloride at each concentration (0.1, 1, 10, 100, 600, 1000, 1200 mM) and 1 mM calcium chloride, the mixture was stirred. Then, luminescence activity was measured with the luminometer Luminescencer-PSN AB2200 (manufactured by Atto Co., Ltd.) for 600 seconds. Table 7 shows the half-lives of luminescence intensity of aequorin at various magnesium chloride concentrations. The light emission patterns of aequorin when it contains magnesium chloride at 0.5 mM, 300 mM, and 600 mM, are shown in FIG. 4.

TABLE 7

| $MgCl_2$ (mM) | $(NH_4)_2SO_4$ (mM) | $CaCl_2$ (mM) | $T_{1/2}$ (min) | Imax (rlu) |
|---|---|---|---|---|
| 0 | 300 | 0.5 | 0.03 | 273684 |
| 0.05 | 300 | 0.5 | 0.03 | 428795 |
| 0.5 | 300 | 0.5 | 0.03 | 248486 |
| 5 | 300 | 0.5 | 0.07 | 494370 |
| 50 | 300 | 0.5 | 0.58 | 186115 |

TABLE 6

| salt | | $(NH_4)_2SO_4$ | | $MgSO_4$ | | $MgCl_2$ | |
|---|---|---|---|---|---|---|---|
| level (mM) | Finalconcentration of $SrCl_2$ added (mM) | $T_{1/2}$ (min) | Imax (rlu) | $T_{1/2}$ (min) | Imax (rlu) | $T_{1/2}$ (min) | Imax (rlu) |
| 1 | 0.5 | 0.02 | 239162 | 0.02 | 308985 | 0.02 | 93133 |
| 10 | 0.5 | 0.02 | 172331 | 0.35 | 342028 | 0.02 | 273963 |
| 100 | 0.5 | 0.02 | 93504 | 1.40 | 103467 | 0.12 | 989553 |
| 300 | 0.5 | 0.03 | 273684 | 2.43 | 57511 | 0.52 | 286940 |
| 600 | 0.5 | 0.12 | 311088 | 13.22 | 10083 | 7.39 | 24720 |
| 1000 | 0.5 | 1.73 | 94581 | 29.90 | 2276 | 25.79 | 4550 |
| 1200 | 0.5 | 11.83 | 15546 | 60.47 | 1061 | 46.73 | 3944 |
| 1500 | 0.5 | 96.95 | 3320 | 198.84 | 528 | 128.40 | 1548 |
| 1500 | 0.0 | — | 41 | — | 27 | — | 27 |
| 0 | 0.0 | — | 31 | — | — | — | — |

AB-2200 background: 6rlu
$T_{1/2}$: Half-life of luminescence intensity
Imax: Maximum luminescence intensity
rlu: Relative luminescence intensity
—: Not measured Table 6 indicates light-emitting time of aequorin lasts longer concentration-dependently when any of the three salts is added. Light emission time of aequorin tended to be extended at 1000 mM for ammonium sulfate, at 100 mM for magnesium sulfate, and at 600 mM for magnesium chloride. Further, it was revealed that the half-life of aequorin luminescence intensity is about 100 min, 200 min, and 130 min in the presence of 1.5 M ammonium sulfate, 1.5 M magnesium sulfate, and 1.5 M magnesium chloride, respectively, indicating that light-emitting time of aequorin was extended drastically longer. Sulfate ions and magnesium ions are TABLE 7-continued

| $MgCl_2$ (mM) | $(NH_4)_2SO_4$ (mM) | $CaCl_2$ (mM) | $T_{1/2}$ (min) | Imax (rlu) |
|---|---|---|---|---|
| 300 | 300 | 0.5 | 2.60 | 67567 |
| 600 | 300 | 0.5 | 10.70 | 8092 |

$T_{1/2}$: Half-life of luminescence intensity
Imax: Maximum luminescence intensity
rlu: Relative luminescence intensity The effect of the interaction between magnesium ions and sulfate ions on extension of light-emitting time of aequorin was examined. As a result, it was shown that light-emitting time becomes longer as the magnesium ion concentration increases above 5 mM. As shown in Table 7, when only 300 mM ammonium sulfate was contained, the half-life of emission time of aequorin was 0.03 min; and as shown in Table 6, when only magnesium chloride was contained, the half-life is 0.52 min. In contrast, when both salts (300 mM each) were contained, the half-life of light-emitting time of aequorin was extended to 2.60 min. Further, when only 600 mM magnesium chloride was contained, the half-life was 7.39 min, whereas both 300 mM ammonium sulfate and 600 mM magnesium chloride were added to the light-emitting reaction system, the half-life of light-emitting time of aequorin was 10.70 min. These findings revealed that magnesium ions are more effective than sulfate ions in the effect of extending light-emitting time of aequorin and that the presence of these two ions enhances the effect of extending light-emitting time of aequorin.

Figure 5:
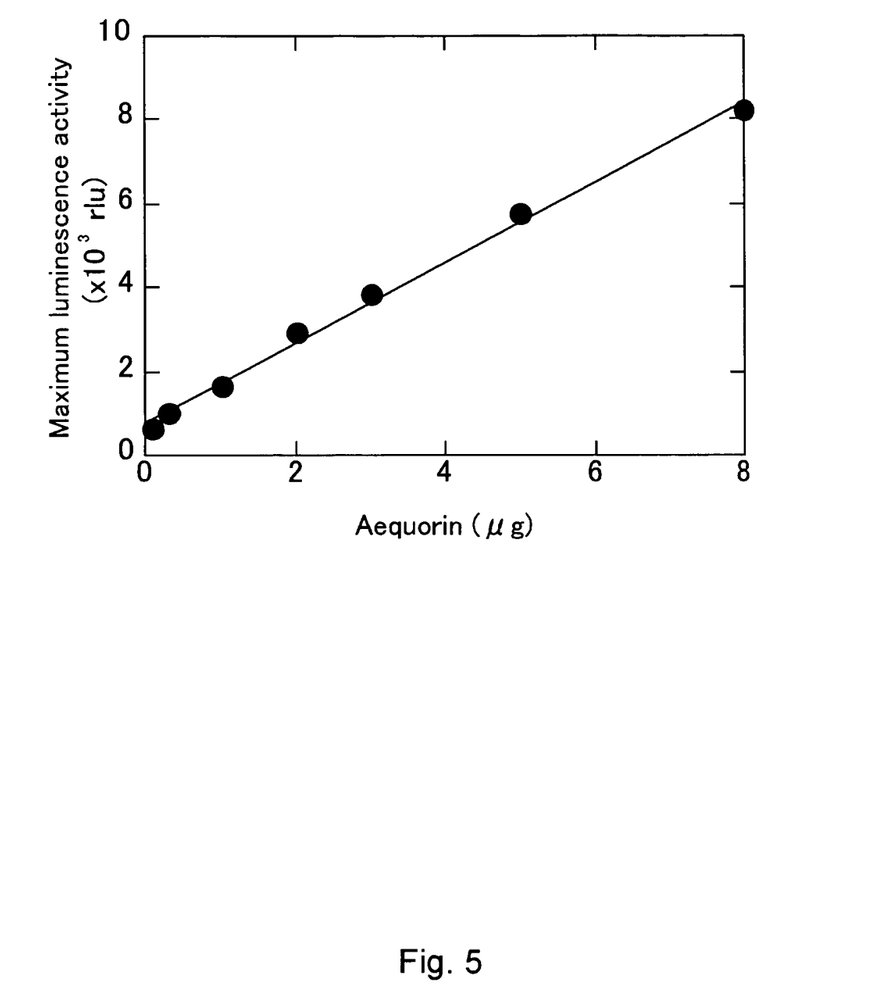
FIG. 5 shows the proportional relationship between the quantity of aequorin and the maximum luminescence intensity in the presence of 1500 mM ammonium sulfate in an example according to the present invention.

(8) Correlation Between the Quantity of the Calcium-Binding Photoprotein Aequorin and Luminescence Intensity A buffer of 10 mM Tris-HCl, pH 7.6, 0.1 mM EDTA containing 1.5 mM ammonium sulfate was prepared. 0.1, 0.3, 1, 2, 3, 5, and 8 µg of aequorin was each added to 100 µl of this solution. After further addition of a buffer (100 µl) of 10 mM Tris-HCl, pH 7.6, 0.1 mM EDTA containing 1 mM calcium chloride and 1.5 M ammonium sulfate, the mixture was stirred. Then, luminescence activity was measured with the luminometer Luminescencer-PSN AB2200 (manufactured by Atto Co., Ltd.) for 600 seconds. FIG. 5 shows the maximum luminescence intensity value for each quantity of aequorins.

It was found that in the presence of 1.5 M ammonium sulfate, luminescence intensity is enhanced in proportion to the quantity of aequorin. It was thus shown that although luminescence intensity decreases in the presence of salts such as ammonium sulfate, magnesium sulfate, and magnesium chloride, compared with the intensity of instantaneous light emission of aequorin, strong luminescence intensity can be obtained by increasing the quantity of aequorins.

(9) Method for Extending Light Emission Time of Semi-Synthesized Calcium-Binding Photoprotein Aequorins by Addition of Various Salts The effect of extending light-emitting time of the semi-synthesized aequorins (h-aequorin and e-aequorin) was examined using ammonium sulfate, magnesium sulfate, or magnesium chloride, all of which exhibited a remarkable effect in extending light-emitting time of aequorin. A buffer of 10 mM Tris-HCl, pH 7.6, 0.1 mM EDTA, containing each salt at 1.5 M, was prepared. 1.0 µg of a semi-synthesized aequorin (h-aequorin or e-aequorin) was added to 100 µl of the salt-containing solution (100 µl). After further addition of 100 µl of 1.5 M ammonium sulfate, magnesium sulfate, or magnesium-chloride solution containing 1 mM calcium chloride, the mixture was stirred. Then, luminescence activity was measured with the luminometer Luminescencer-PSN AB2200 (manufactured by Atto Co., Ltd.) for 600 seconds. Table 8 shows the half-lives of luminescence intensity and maximum luminescence intensities of aequorin in the presence of various salts.

TABLE 8

| Semi-synthesized aequorin | Final concentration of CaCl$_2$ added (mM) | 1.5M (NH$_4$)$_2$SO$_4$ | | 1.5M MgSO$_4$ | | 1.5M MgCl$_2$ | |
|---|---|---|---|---|---|---|---|
| | | T$_{1/2}$ (min) | Imax (rlu) | T$_{1/2}$ (min) | Imax (rlu) | T$_{1/2}$ (min) | Imax (rlu) |
| h-Aequorin | 0.5 | 9.31 | 6163 | 16.57 | 2732 | 7.79 | 7716 |
| e-Aequorin | 0.5 | 17.72 | 631 | 39.15 | 209 | 24.92 | 650 |

T$_{1/2}$: Half-life of luminescence intensity
Imax: Maximum luminescence intensity
rlu: Relative luminescence intensity As a result of comparison of half-lives of the luminescence intensity of the semi-synthesized aequorins in the presence of 1.5 M ammonium sulfate, magnesium sulfate, or magnesium chloride, light-emitting time of the semi-synthesized aequorins tended to be extended in the presence of any of the three salts. It is suggested that, as in the case of aequorin, sulfate ions and magnesium ions play an important role in the effect of extending light-emitting time of semi-synthesized aequorins.

What is claimed is:

1. A method for extending light-emitting time of a solution comprising (a) a calcium-binding photoprotein that requires a calcium ion for producing luminescence and that is composed of an apoprotein and peroxide of coelenterazine or analog thereof and (b) a calcium ion, cadmium ion, and/or lead ion, the method comprising:
   (i) providing a solution comprising the calcium-binding photoprotein wherein the concentration of the calcium-binding photoprotein is 0.01 mg/ml to 10 mg/ml;
   (ii) stirring a magnesium ion or a zinc ion with the solution in (i) such that the concentration of the magnesium ion after stirring is 10 mM or more or the concentration of the zinc ion after stirring is 600 mM or more;
   (iii) stirring a calcium ion, cadmium ion, and/or lead ion with the solution comprising the calcium-binding photoprotein such that the concentration of the calcium ion or another cation that can be substituted for the calcium ion is $10^{-7}$ mole/liter or more; and
   (iv) allowing a reaction between (a) and (b) to proceed in the solution obtained in (iii);
   wherein during the light-emitting time, (a) binds to (b) to bring about oxidation of the peroxide of a coelenterazine or an analog thereof, resulting in the release of a coelenteramide or an analog thereof from the apoprotein.

2. A method of extending light-emitting time of a solution comprising (a) a calcium-binding photoprotein that requires a calcium ion for producing luminescence and that is composed of an apoprotein and peroxide of coelenterazine or analog thereof and (b) a calcium ion cadmium ion, and/or lead ion, the method comprising:
   (i) providing a solution comprising the calcium-binding photoprotein wherein the concentration of the calcium-binding photoprotein is 0.01 mg/ml to 10 mg/ml;
   (ii) stirring a sulfate ion and either a magnesium ion or a zinc ion with the solution in (i) such that the concentration of the sulfate ion after stirring is 300 mM or more and the concentration of the magnesium ion after stirring is 5 mM or more or the concentration of the zinc ion after stirring is 600 mM or more;
   (iii) stirring a calcium ion, cadmium ion, and/or lead ion with the solution comprising the calcium-binding photoprotein such that the concentration of the calcium ion or another cation that can be substituted for the calcium ion is $10^{-7}$ mole/liter or more; and
   (iv) allowing a reaction between (a) and (b) to proceed in the solution obtained in (iii);
   wherein during the light-emitting time, (a) binds to (b) to bring about oxidation of the peroxide of a coelenterazine or an analog thereof, resulting in the release of a coelenteramide or an analog thereof from the apoprotein.

3. The method of claim 1, wherein the coelenterazine or the analog thereof is represented in the following formula (1) or (2):

wherein
   $R^1$ is a substituted or unsubstituted aryl group, a substituted or unsubstituted arylated alkyl group, or a straight or branched chain alkyl group that may be substituted for an aliphatic cyclic group;
   $R^2$ is a substituted or unsubstituted aryl group, a substituted or unsubstituted arylated alkyl group, a substituted or unsubstituted aryl alkenyl group, a straight or branched chain alkyl group that may be substituted for an aliphatic cyclic group, a straight or branched chain alkenyl group that may be substituted for an aliphatic cyclic group, or a heterocyclic group;
   $R^3$ is a hydrogen atom, or a substituted or unsubstituted alkyl group;
   $X^1$ is a hydrogen atom, a hydroxyl group, a halogen atom, an alkoxyl group, or an amino group;
   $X^2$ is a hydrogen atom or a hydroxyl group; and
   Y is a divalent hydrocarbon group having 1 to 4 carbon atoms.

4. The method of claim 3,
   wherein, in the formula (1) or formula (2),
   $R^1$ is an unsubstituted aryl group, an unsubstituted arylated alkyl group, an arylated alkyl group substituted for a hydroxyl group or a halogen atom, or a straight or branched chain alkyl group that may be substituted for a cyclohexyl group;

$R^2$ is an unsubstituted aryl group, an aryl group substituted for a hydroxyl group, an unsubstituted arylated alkyl group, an arylated alkyl group substituted for a hydroxyl group, an unsubstituted aryl alkenyl group, an unsubstituted straight or branched chain alkyl group, a straight chain alkyl group that may be substituted for an aliphatic cyclic group, a branched chain alkenyl group, or a heterocyclic group containing sulfur;

$R^3$ is a hydrogen atom, a methyl group, or 2-hydroxyethyl group;

$X^1$ is a hydrogen atom, a hydroxyl group, a fluorine atom, a methoxy group, or an amino group;

$X^2$ is a hydrogen atom or a hydroxyl group; and

Y is a methylene group, ethylene group, a propylene group, or a vinylene group.

5. The method of claim 4,
wherein, in the formula (1) or (2),
$R^1$ is a phenyl group, a benzyl group, a p-hydroxybenzyl group, a p-fluorobenzyl group, a p-chlorobenzyl group, a p-bromobenzyl group, a p-iodinebenzyl group, a 3,4-difluorobenzyl group, a pentafluorobenzyl group, a phenylethyl group, a phenylpropyl group, a naphthylmethyl group, a cyclohexylmethyl group, a methyl group, a 1-methylpropyl group, or a 2-methylpropyl group;
and $R^2$ is a phenyl group, a p-hydroxy phenyl group, a benzyl group, an α-hydroxybenzyl group, a phenylethyl group, a phenylvinyl group, a cyclohexyl group, a cyclohexylmethyl group, a cyclohexylethyl group, a methyl group, an ethyl group, a propyl group, a 2-methylpropyl group, a 2-methylpropenyl group, an adamantylmethyl group, a cyclopentylmethyl group, or a thiophene-2-yl group.

6. The method of claim 1, wherein, in a molecule of the calcium-binding photoprotein, the ratio of the number of molecules of the apoprotein to the number of molecules of the peroxide of the coelenterazine or the analog thereof is 1:1.

7. The method of claim 1, wherein the apoprotein is an apoprotein having the amino acid sequence shown in any one of SEQ ID NOs: 1 to 4.

8. The method of claim 1, wherein the calcium-binding photoprotein is a protein selected from the group consisting of aequorin, clytin, obelin, mitrocomin, mineopsin, and bervoin.

9. The method of claim 1, wherein the calcium-binding photoprotein is a protein selected from the group consisting of aequorin, clytin, obelin, mitrocomin, mineopsin, and bervoin.

10. A method for extending light-emitting time of a solution comprising (a) a calcium-binding photoprotein that requires a calcium ion for producing luminescence and that is composed of an apoprotein and peroxide of coelenterazine or analog thereof and (b) a calcium ion cadmium ion, and/or lead ion, the method comprising:
   (i) providing a solution comprising the calcium-binding photoprotein wherein the concentration of the calcium-binding photoprotein is 0.01 mg/ml to 10 mg/ml;
   (ii) stirring magnesium sulfate, magnesium chloride, zinc sulfate, zinc chloride, or strontium chloride, with the solution in (i) such that the concentration of magnesium sulfate after stirring is 10 mM or more, the concentration of magnesium chloride after stirring is 300 mM or more, the concentration of zinc sulfate after stirring is 600 mM or more, the concentration of zinc chloride after stirring is 600 mM or more, or the concentration of strontium chloride after stirring is 600 mM or more; and
   (iii) stirring a calcium ion, cadmium ion, and/or lead ion with the solution comprising the calcium-binding photoprotein such that the concentration of the calcium ion or another cation that can be substituted for the calcium ion is $10^{-7}$ mole/liter or more;
   (iv) allowing a reaction between (a) and (b) to proceed in the solution obtained in (iii);
   wherein during the light-emitting time, (a) binds to (b) to bring about oxidation of the peroxide of a coelenterazine or an analog thereof, resulting in the release of a coelenteramide or an analog thereof from the apoprotein.

11. The method of claim 10, wherein the coelenterazine or the analog thereof is represented in the following formula (1) or (2):

(1)

(2)

wherein $R^1$ is a substituted or unsubstituted aryl group, a substituted or unsubstituted arylated alkyl group, or a straight or branched chain alkyl group that may be substituted for an aliphatic cyclic group;

$R^2$ is a substituted or unsubstituted aryl group, a substituted or unsubstituted arylated alkyl group, a substituted or unsubstituted aryl alkenyl group, a straight or branched chain alkyl group that may be substituted for an aliphatic cyclic group, a straight or branched chain alkenyl group that may be substituted for an aliphatic cyclic group, or a heterocyclic group;

$R^3$ is a hydrogen atom, or a substituted or unsubstituted alkyl group;

$X^1$ is a hydrogen atom, a hydroxyl group, a halogen atom, an alkoxyl group, or an amino group;

$X^2$ is a hydrogen atom or a hydroxyl group; and

Y is a divalent hydrocarbon group having 1 to 4 carbon atoms.

12. The method of claim 2, wherein the coelenterazine or the analog thereof is represented in the following formula (1) or (2):

wherein
- $R^1$ is a substituted or unsubstituted aryl group, a substituted or unsubstituted arylated alkyl group, or a straight or branched chain alkyl group that may be substituted for an aliphatic cyclic group;
- $R^2$ is a substituted or unsubstituted aryl group, a substituted or unsubstituted arylated alkyl group, a substituted or unsubstituted aryl alkenyl group, a straight or branched chain alkyl group that may be substituted for an aliphatic cyclic group, a straight or branched chain alkenyl group that may be substituted for an aliphatic cyclic group, or a heterocyclic group;
- $R^3$ is a hydrogen atom, or a substituted or unsubstituted alkyl group;
- $X^1$ is a hydrogen atom, a hydroxyl group, a halogen atom, an alkoxyl group, or an amino group;
- $X^2$ is a hydrogen atom or a hydroxyl group; and
- Y is a divalent hydrocarbon group having 1 to 4 carbon atoms.

13. The method of claim 11, wherein, in the formula (1) or formula (2),
- $R^1$ is an unsubstituted aryl group, an unsubstituted arylated alkyl group, an arylated alkyl group substituted for a hydroxyl group or a halogen atom, or a straight or branched chain alkyl group that may be substituted for a cyclohexyl group;
- $R^2$ is an unsubstituted aryl group, an aryl group substituted for a hydroxyl group, an unsubstituted arylated alkyl group, an arylated alkyl group substituted for a hydroxyl group, an unsubstituted aryl alkenyl group, an unsubstituted straight or branched chain alkyl group, a straight chain alkyl group that may be substituted for an aliphatic cyclic group, a branched chain alkenyl group, or a heterocyclic group containing sulfur;
- $R^3$ is a hydrogen atom, a methyl group, or 2-hydroxyethyl group;
- $X^1$ is a hydrogen atom, a hydroxyl group, a fluorine atom, a methoxy group, or an amino group;
- $X^2$ is a hydrogen atom or a hydroxyl group; and
- Y is a methylene group, ethylene group, a propylene group, or a vinylene group.

14. The method of claim 12, wherein, in the formula (1) or formula (2),
- $R^1$ is an unsubstituted aryl group, an unsubstituted arylated alkyl group, an arylated alkyl group substituted for a hydroxyl group or a halogen atom, or a straight or branched chain alkyl group that may be substituted for a cyclohexyl group;
- $R^2$ is an unsubstituted aryl group, an aryl group substituted for a hydroxyl group, an unsubstituted arylated alkyl group, an arylated alkyl group substituted for a hydroxyl group, an unsubstituted aryl alkenyl group, an unsubstituted straight or branched chain alkyl group, a straight chain alkyl group that may be substituted for an aliphatic cyclic group, a branched chain alkenyl group, or a heterocyclic group containing sulfur;
- $R^3$ is a hydrogen atom, a methyl group, or 2-hydroxyethyl group;
- $X^1$ is a hydrogen atom, a hydroxyl group, a fluorine atom, a methoxy group, or an amino group;
- $X^2$ is a hydrogen atom or a hydroxyl group; and
- Y is a methylene group, ethylene group, a propylene group, or a vinylene group.

* * * * *